(12) United States Patent
Zhang et al.

(10) Patent No.: US 9,053,291 B2
(45) Date of Patent: Jun. 9, 2015

(54) CONTINUOUS ANNEALING PROCESS FAULT DETECTION METHOD BASED ON RECURSIVE KERNEL PRINCIPAL COMPONENT ANALYSIS

(75) Inventors: Yingwei Zhang, Shenyang (CN); Teng Yongdong, Shenyang (CN); Hu Zhiyong, Shenyang (CN)

(73) Assignees: Northeastern University, Shenyang, Liaoning Province (CN); Yingwei Zhang, Shenyang, Liaoning Province (CN); Yongdong Teng, Shenyang, Liaoning Province (CN); Zhyong Hu, Shenyang, Liaoning Province (CN)

( * ) Notice: Subject to any disclaimer, the term of this patent is extended or adjusted under 35 U.S.C. 154(b) by 541 days.

(21) Appl. No.: 13/391,775

(22) PCT Filed: Sep. 29, 2010

(86) PCT No.: PCT/CN2010/077441
§ 371 (c)(1),
(2), (4) Date: Feb. 22, 2012

(87) PCT Pub. No.: WO2012/040916
PCT Pub. Date: Apr. 5, 2012

(65) Prior Publication Data
US 2013/0035910 A1 Feb. 7, 2013

(51) Int. Cl.
*G06F 17/10* (2006.01)
*G06F 19/00* (2011.01)
(52) U.S. Cl.
CPC ................................. *G06F 19/707* (2013.01)
(58) Field of Classification Search
None
See application file for complete search history.

(56) References Cited

U.S. PATENT DOCUMENTS 6,952,657 B2 * 10/2005 Jahns et al. .................... 702/182
7,248,939 B1 * 7/2007 Chamness et al. ............. 700/121
7,421,351 B2 * 9/2008 Navratil ........................... 702/58
(Continued)

FOREIGN PATENT DOCUMENTS

CN       1655082 A     8/2005
CN    101446831 A     6/2009

OTHER PUBLICATIONS

Y. Zhang, Y. Teng, "Adaptive multiblock kernel principal component analysis for monitoring complex industrial process" pp. 948-955, 2010.*

(Continued)

*Primary Examiner* — Kibrom K Gebresilassie
(74) *Attorney, Agent, or Firm* — Muncy, Geissler, Olds & Lowe, P.C.

(57) ABSTRACT

A fault detection method in a continuous annealing process based on a recursive kernel principal component analysis (RKPCA) is disclosed. The method includes: collecting data of the continuous annealing process including roll speed, current and tension of an entry loop (ELP); building a model using the RKPCA and updating the model, and calculating the eigenvectors $\hat{P}$. In the fault detection of the continuous annealing process, when the $T^2$ statistic and SPE statistic are greater than their confidence limit, a fault is identified; on the contrary, the whole process is normal. The method mainly solves the nonlinear and time-varying problems of data, updates the model and calculates recursively the eigenvalues and eigenvectors of the training data covariance by the RKPCA. The results show that the method can not only greatly reduce false alarms, but also improve the accuracy of fault detection.

3 Claims, 5 Drawing Sheets

(56) References Cited

U.S. PATENT DOCUMENTS

| | | | |
|---|---|---|---|
| 8,620,519 B2* | 12/2013 | Mukherjee et al. | 701/32.9 |
| 2005/0055175 A1* | 3/2005 | Jahns et al. | 702/182 |
| 2007/0282777 A1 | 12/2007 | Guralnik et al. | |
| 2011/0066391 A1* | 3/2011 | AbuAli et al. | 702/61 |
| 2011/0284512 A1* | 11/2011 | Stork Genannt Wersborg | 219/121.72 |
| 2012/0065948 A1* | 3/2012 | Tan et al. | 703/2 |
| 2013/0110422 A1* | 5/2013 | Zhang et al. | 702/58 |

OTHER PUBLICATIONS

M. H. Nguyen, F. D. Torre, "Robust Kernel Principal Component Analysis" pp. 1-8, 2009.*

Y. Zhang, S. Li, Y. Teng, "Dynamic processes monitoring using recrusive kernel principal component analysis" pp. 78-86, 2012.*

Y. Zhang, Y. Teng, "Adaptive multiblock kernel principal component analysis for monitoring complex industrial process" pp. 948-955, 2010.*

L. Xie, "Recursive kernel PCA and its application in adaptive monitoring of nonlinear processes" pp. 1776-1782, 2007.*

L. Xie et al., "Recursive kernel PCA and its application in adaptive monitoring of nonlinear processes", *Journal of Chemical Industry and Engineering* (China), vol. 58, No. 7, Jul. 2007, pp. 1776-1782.

W. Li et al., "Recursive PCA for adaptive process monitoring", *Journal of Process Control*, 10 (2000) pp. 471-486.

* cited by examiner

CONTINUOUS ANNEALING PROCESS FAULT DETECTION METHOD BASED ON RECURSIVE KERNEL PRINCIPAL COMPONENT ANALYSIS

BACKGROUND OF THE INVENTION

1. Field of the Invention

The present invention relates to a fault detection and diagnosis, more particular to a fault monitoring method of a continuous annealing process based on recursive kernel principal component analysis.

2. The Prior Arts

With increasing complexity of industrial processes, the requirement for reliability, availability and security is growing significantly. Fault detection and diagnosis (FDD) are becoming a major issue in industry. The actual production process has different characteristics, like linear, nonlinear, time-invariant, time-varying, etc. For the different production processes, we should use different fault monitoring methods so as to effectively monitor the fault. Continuous annealing process is a complex time-varying nonlinear process.

For nonlinear characteristics of the industrial process, some scholars have proposed a kernel principal analysis (KPCA) method. KPCA projects nonlinear data to high-dimensional feature space by nonlinear kernel function, then performs a linear PCA feature extraction in the feature space. KPCA is to perform PCA in high-dimensional feature space, which is not necessary for solving nonlinear optimization problems, and compared with other nonlinear methods it does not need to specify the number of the principal component before modeling, but KPCA method has disadvantage. KPCA is an approach based on the data covariance structure where the principal component model is time-invariant. In the actual industrial process, the mean, variance, correlation structure of process variables under normal conditions will be changed slowly due to sensor drift, equipment aging, raw material change and reduced catalyst activity, etc. Compared with the process fault the changes are slow, which belongs to the normal process operation. When the time-invariant principal component model is applied to time-varying process, it may cause false alarms. Therefore it is necessary to propose a feasible method to solve the time-varying nonlinear problems.

SUMMARY OF THE INVENTION

To solve the time-varying nonlinear problems, the invention proposes a fault monitoring method in a continuous annealing process based on recursive kernel principal component analysis to achieve the purpose of reducing false alarm rate.

The technical solution of the present invention is implemented as follows: The fault detection method in the continuous annealing process based on a recursion kernel principal component analysis (RKPCA) includes the following steps:

Step 1: Collect data and standardize the data, collecting data in the continuous annealing industrial process including: the roll speed, current and tension of an entry loop (ELP);

Step 2: Calculate the principal factors P of fault in the continuous annealing process, i.e., build an initial monitoring model of the continuous annealing process with N standardized samples in Step 1. Monitor a new sample $x_{new}$ of the continuous annealing process. If it is abnormal, an alarm will be given, otherwise go to Step 3;

Where, the extracted principal factor P in the continuous annealing process is as follows:

$$P = \Phi(X) \begin{bmatrix} \frac{1}{h_\Phi}\sqrt{\frac{N-1}{N(N-2)}} & 0^T \\ -\frac{1}{h_\Phi}\sqrt{\frac{N-1}{N(N-2)}} B & \tilde{A} \end{bmatrix} U'_\Phi$$

Here $\Phi(X)$ is a mapping matrix of N samples $X=[x_1, x_2, \ldots, x_N]$. N is the sample number, the regulating factor of initial monitoring model in the continuous annealing process is $$h_\Phi = \frac{N-1}{N(N-2)}\sqrt{1 - 2B^T k(X, x_1) + B^T K(X) B},$$

the correcting matrix of initial monitoring model in the continuous annealing process is $$B = \frac{1}{N-1} 1_{N-1} + \tilde{A}\tilde{\Lambda}\tilde{A}^T \left( k(\tilde{X}, x_1) - \frac{1}{N-1} K(\tilde{X}) 1_{N-1} \right),$$

$k(X, x_1)$ indicates the inner product of X and $x_1$. $K(X)$ indicates the inner product of the sample matrix. $k(\tilde{X}, x_1)$ is the inner product of $\tilde{X}$ and $x_1$, $\tilde{X}$ is the middle matrix, $K(\tilde{X})$ indicates the inner product of the middle matrix, $\tilde{\Lambda}$ is the eigenvalues matrix of the middle covariance matrix, $U_\Phi'$ is the eigenvectors matrix of the process variables, $1_{N-1}$ is the unit vector in N−1 column;

Extract the transmission factor of the continuous annealing process, which is expressed as:

$$\begin{bmatrix} \frac{1}{h_\Phi}\sqrt{\frac{N-1}{N(N-2)}} & 0^T \\ -\frac{1}{h_\Phi}\sqrt{\frac{N-1}{N(N-2)}} B & \tilde{A} \end{bmatrix} = A(U'_\Phi)^{-1}$$

Step 3: When the continuous annealing process sample $x_{new}$ is normal data, we use the recursive kernel principal component analysis (RKPCA) in Step 2 to update the initial monitoring model of the continuous annealing process, and calculate the principal factor $\hat{P}$ of the fault in the updated continuous annealing process model. $\hat{P}$ is expressed as follows:

$$\hat{P} = \Phi([\tilde{X} \; x_{new}]) \begin{bmatrix} \tilde{A} & -\frac{1}{h'_\Phi}\sqrt{\frac{N-1}{N(N-2)}} B' \\ 0^T & \frac{1}{h'_\Phi}\sqrt{\frac{N-1}{N(N-2)}} \end{bmatrix} U''_\Phi = \Phi(X_{new})\hat{A}$$

where $\Phi(X_{new})=\Phi([\tilde{X} \; x_{new}])$ is the updated mapping matrix. The regulating factor for the updated monitoring model in the continuous annealing process is $$h'_\Phi = \frac{N-1}{N(N-2)}\sqrt{1 - 2B'^T k(\tilde{X}, x_{new}) + B'^T K(\tilde{X})B'},$$

the regulating matrix for the updating monitoring model in the continuous annealing process is $$B' = \frac{1}{N-1}1_{N-1} + \tilde{A}\tilde{\Lambda}\tilde{A}^T\left(k(\tilde{X}, x_{new}) - \frac{1}{N-1}K(\tilde{X})1_{N-1}\right),$$

$k(\tilde{X}, x_{new})$ $$m_\Phi = \frac{1}{N}\Phi([x_1 \ \tilde{X}])1_N = \frac{1}{N}\Phi(x_1) + \frac{N-1}{N}\tilde{m}_\Phi$$

$$C^F = \frac{1}{N-1}\Phi([x_1 \ \tilde{X}])\Phi([x_1 \ \tilde{X}])^T$$

indicates the inner product of $\tilde{X}$ and $x_{new}$.

Step 4: Detect Fault for the Continuous Annealing Process.

The fault of the continuous annealing process can be judged by using Hotelling's $T^2$ statistic and squared prediction error (SPE) statistic. When the $T^2$ statistic and SPE statistic exceed their confidence limit, a failure is identified; on the contrary, the whole process is normal, go to step 3 to continue to update the initial monitoring model of the continuous annealing process.

Step 2 describes that an initial model of the continuous annealing process using the first N samples after standardizing in Step 1 is built, and includes the following steps:

RKPCA method proposed by the invention updates recursively eigenvalues in the feature space of the sample covariance matrix. Let $X=[x_1, x_2, \ldots, x_N]$ be the sample matrix of the continuous annealing process, $x_1, x_2, \ldots, x_N$ are the samples of the continuous annealing process, N is the sample number, $\tilde{X}=[x_2, \ldots, x_N]\in R^{m\times(N-1)}$ is the middle matrix of the continuous annealing process, m is the number of sampling variables in the continuous annealing process, $X_{new}=[\tilde{X}\ x_{new}]$ is the sample matrix of updating model in the continuous annealing process, $x_{new}$ is the new sample of the continuous annealing process. After mapping X, $\tilde{X}$ and $X_{new}$ to the high-dimensional feature space, they are $\Phi(X)$, $\Phi(\tilde{X})$ and $\Phi(X_{new})$ respectively. So the mean vector $m_\Phi$ and covariance matrix $C^F$ of $\Phi(X)$ can be calculated $$m_\Phi = \frac{1}{N}\Phi([x_1 \ \tilde{X}])1_N = \frac{1}{N}\Phi(x_1) + \frac{N-1}{N}\tilde{m}_\Phi \quad (1)$$

$$C^F = \frac{1}{N-1}\Phi([x_1 \ \tilde{X}])\Phi([x_1 \ \tilde{X}])^T$$

$$= \frac{1}{N-1}(\Phi(x_1) - m_\Phi)(\Phi(x_1) - m_\Phi)^T + \frac{1}{N-1}\sum_{i=2}^{N}$$

$$(\Phi(x_i) - m_\Phi)(\Phi(x_i) - m_\Phi)^T$$

$$= \frac{1}{N-1}\left[\frac{N-1}{N}\Phi(x_1) - \frac{N-1}{N}\tilde{m}_\Phi\right]$$

$$\left[\frac{N-1}{N}\Phi(x_1) - \frac{N-1}{N}\tilde{m}_\Phi\right]^T + \frac{1}{N-1}\sum_{i=2}^{N}$$

$$\left[\Phi(x_i) - \tilde{m}_\Phi + \frac{1}{N}\tilde{m}_\Phi - \frac{1}{N}\Phi(x_1)\right]\times$$

$$\left[\Phi(x_i) - \tilde{m}_\Phi + \frac{1}{N}\tilde{m}_\Phi - \frac{1}{N}\Phi(x_1)\right]^T$$

$$= \frac{1}{N}(\Phi(x_1) - \tilde{m}_\Phi)(\Phi(x_1) - \tilde{m}_\Phi)^T + \frac{1}{N-1}\sum_{i=2}^{N}$$

$$(\Phi(x_i) - \tilde{m}_\Phi)(\Phi(x_i) - \tilde{m}_\Phi)^T$$

$$= \frac{1}{N}(\Phi(x_1) - \tilde{m}_\Phi)(\Phi(x_1) - \tilde{m}_\Phi)^T + \frac{N-2}{N-1}\tilde{C}^F$$

$$= \frac{N-2}{N-1}\left[\sqrt{\frac{N-1}{N(N-2)}}(\Phi(x_1) - \tilde{m}_\Phi) \ \sqrt{\frac{1}{N-2}}\Phi(\tilde{X})\right]\times \quad (2)$$

$$\left[\sqrt{\frac{N-1}{N(N-2)}}(\Phi(x_1) - \tilde{m}_\Phi) \ \sqrt{\frac{1}{N-2}}\Phi(\tilde{X})\right]$$

where $\tilde{m}_\Phi$ and $\tilde{C}^F$ represent the mean vector and covariance matrix of $\Phi(\tilde{X})$, respectively. $\overline{\Phi}([x_1 \ \tilde{X}])$ is the mean matrix of $\Phi(X)$, $1_N$ is a row vector consisting of 1 with the number of N, $\Phi(x_i)$ is the mapping vector to the high-dimensional feature space of $x_i$, $i=1 \ldots N$, $\overline{\Phi}(\tilde{X})$ is the mean matrix of $\Phi(\tilde{X})$;

$\Lambda$ and P are the eigenvalues matrix and the main factors of $C^F$, respectively. $\tilde{\Lambda}$ and $\tilde{P}$ are the eigenvalues matrix and the main factors of covariance matrix $\tilde{C}^F$ of $\Phi(\tilde{X})$, respectively. Assume $\tilde{P}=PR_\Phi$, $R_\Phi$ is an orthogonal rotation matrix. Due to $P=\Phi(X)A$, $\tilde{P}=\Phi(\tilde{X})\tilde{A}$, where $A=(I-(1/N)\times E_N)[v_1/\sqrt{\xi_1}, v_2/\sqrt{\xi_2}, \ldots, v_i/\sqrt{\xi_i}]$, $\xi_i$ and $v_i$ indicate the ith eigenvalues and eigenvectors of $\overline{\Phi}(X)^T\overline{\Phi}(x)$, respectively. $\tilde{A}=(I-(1/(N-1))\times E_{N-1})[\tilde{v}_1/\sqrt{\omega_1}, \tilde{v}_2/\sqrt{\omega_2}, \ldots, \tilde{v}_i/\sqrt{\omega_i}]$, $\omega_i$ and $\tilde{v}_i$ indicate the ith eigenvalues and eigenvectors of $\overline{\Phi}(\tilde{X})^T\overline{\Phi}(\tilde{X})$, we can get $P^T C^F P = \Lambda$ and $\tilde{P}^T \tilde{C}^F \tilde{P} = \tilde{\Lambda}$ by diagonalizing $C^F$ and $\tilde{C}^F$, respectively. We can get $[(N-1)/(N-2)]\Lambda - [(N-1)/(N(N-2))]g_\Phi g_\Phi^T = R_\Phi \tilde{\Lambda} R_\Phi^T$ from Equation (2), wherein $g_\Phi = P^T(\Phi(x_1) - \tilde{m}_\Phi) = A^T[k(X,x_1) - (1/(N-1))K(X, \tilde{X})1_{N-1}]$; Let $S_\Phi = [(N-1)/(N-2)]\Lambda - [(N-1)/(N(N-2))]g_\Phi g_\Phi^T$, $\tilde{\Lambda}$ and $R_\Phi$ are the eigenvalues matrix and eigenvectors matrix of $S_\Phi$, we get Equation (3) from Equation (2).

$$P^T C^F P = \frac{1}{N}P^T(\Phi(x_1) - \tilde{m}_\Phi)(\Phi(x_1) - \tilde{m}_\Phi)^T P + \frac{N-2}{N-1}P^T \tilde{C}^F P \quad (3)$$

$$= \frac{1}{N}g_\Phi g_\Phi^T + \frac{N-2}{N-1}A^T\Phi(X)^T\tilde{P}\tilde{\Lambda}\tilde{P}^T\Phi(X)A$$

$$= \frac{1}{N}g_\Phi g_\Phi^T + \frac{N-2}{N-1}A^T\Phi(X)^T\Phi(\tilde{X})\tilde{A}\tilde{\Lambda}\tilde{A}^T\Phi(\tilde{X})^T\Phi(X)A$$

$$= \frac{1}{N}g_\Phi g_\Phi^T + \frac{N-2}{N-1}A^T K(X, \tilde{X})\tilde{A}\tilde{\Lambda}\tilde{A}^T K(X, \tilde{X})^T A$$

$$= \Lambda$$

where $K(X,\tilde{X})$ indicates the inner product of sample matrix and middle matrix in the continuous annealing process;

The singular value decomposition in Equation (2) satisfies:

$$\sqrt{\frac{1}{N-2}}\Phi(\tilde{X}) = \tilde{P}\sum_\Phi \tilde{D}_\Phi^T \quad (4)$$

where $\tilde{P}=\Phi(\tilde{X})\tilde{A}$ is the main factor of $\tilde{C}^F$, $\tilde{\Sigma}_\Phi$ is the diagonal matrix and satisfies $\tilde{\Sigma}_\Phi^2 = \tilde{\Lambda}$. $\tilde{D}_\Phi$ is the corresponding right-singular matrix. From Equations (4) and (2), we have:

$$\left[\sqrt{\frac{N-1}{N(N-2)}}(\Phi(x_1)-\tilde{m}_\Phi)\sqrt{\frac{1}{N-2}}\Phi(\tilde{X})\right] = \quad (5)$$

$$[u_\Phi \ \tilde{P}]\begin{bmatrix} h_\Phi & 0^T \\ \tilde{A}\tilde{P}^T\sqrt{\frac{N-1}{N(N-2)}}(\Phi(x_1)-\tilde{m}_\Phi) & \tilde{\Sigma}_\Phi \end{bmatrix}\begin{bmatrix} 1 & 0^T \\ 0_{N-1} & \tilde{D}_\Phi \end{bmatrix}^T =$$

$$[u_\Phi \ \tilde{P}]\begin{bmatrix} h_\Phi & 0^T \\ \tilde{A}R_\Phi^T P^T\sqrt{\frac{N-1}{N(N-2)}}(\Phi(x_1)-\tilde{m}_\Phi) & \tilde{\Sigma}_\Phi \end{bmatrix}\begin{bmatrix} 1 & 0^T \\ 0_{N-1} & \tilde{D}_\Phi \end{bmatrix}^T$$

where the regulating factor of the initial monitoring model in the continuous annealing process:

$$h_\Phi = \left\|(I - \tilde{P}\tilde{A}\tilde{P}^T)\sqrt{\frac{N-1}{N(N-2)}}(\Phi(x_1)-\tilde{m}_\Phi)\right\| \quad (6)$$

$$= \sqrt{\frac{N-1}{N(N-2)}}\|(I - \tilde{P}\tilde{A}\tilde{P}^T)(\Phi(x_1)-\tilde{m}_\Phi)\|$$

$$= \sqrt{\frac{N-1}{N(N-2)}}\left\|\Phi(x_1) - \frac{1}{N-1}\Phi(\tilde{X})1_{N-1} - \Phi(\tilde{X})\tilde{A}\tilde{A}^T\left(\Phi(\tilde{X})^T\Phi(x_1) - \frac{1}{N-1}\Phi(\tilde{X})^T\Phi(\tilde{X})1_{N-1}\right)\right\|$$

$$= \frac{N-1}{N(N-2)}\left\|\Phi(x_1) - \frac{1}{N-1}\Phi(\tilde{X})1_{N-1} - \Phi(\tilde{X})\tilde{A}\tilde{A}^T\left(k(\tilde{X},x_1) - \frac{1}{N-1}K(\tilde{X})1_{N-1}\right)\right\|$$

$$\frac{N-1}{N(N-2)}\|\Phi(x_1)-\Phi(\tilde{X})B\|$$

$$= \sqrt{\frac{N-1}{N(N-2)}}\sqrt{1 - 2B^T k(\tilde{X},x_1) + B^T K(\tilde{X})B}$$

$$u_\Phi = \frac{1}{h_\Phi}\sqrt{\frac{N-1}{N(N-2)}}(I-\tilde{P}\tilde{A}\tilde{P}^T)(\Phi(x_1)-\tilde{m}_\Phi) \quad (7)$$

$$= \frac{1}{h_\Phi}\sqrt{\frac{N-1}{N(N-2)}}[\Phi(x_1)-\Phi(\tilde{X})B]$$

The correcting matrix of the main factors for the initial model in the continuous annealing process:

$$B = \frac{1}{N-1}1_{N-1} + \tilde{A}\tilde{A}^T\left(k(\tilde{X},x_1) - \frac{1}{N-1}K(\tilde{X})1_{N-1}\right) \quad (8)$$

where $K(\tilde{X})$ indicates the inner product of the middle matrix in the continuous annealing process, $k(\tilde{X}, x_1)$ indicates the inner product of $\tilde{X}$ and $x_1$;

Set $$V_\Phi = \begin{bmatrix} h_\Phi & 0^T \\ \tilde{A}R_\Phi^T P^T\sqrt{\frac{N-1}{N(N-2)}}(\Phi(x_1)-\tilde{m}_\Phi) & \tilde{\Sigma}_\Phi \end{bmatrix}$$

$$= \begin{bmatrix} h_\Phi & 0^T \\ \tilde{A}R_\Phi^T P^T\sqrt{\frac{N-1}{N(N-2)}}\left(k(X,x_1) - \frac{1}{N-1}K(X,\tilde{X})1_{N-1}\right) & \tilde{\Sigma}_\Phi \end{bmatrix}$$

We get $V_\Phi = U_\Phi'\Sigma_\Phi'D_\Phi'^T$ by singular value decomposition of $V_\Phi$. $U_\Phi'$ is the eigenvectors matrix, $\Sigma_\Phi'$ is the diagonal matrix, $D_\Phi'$ is the corresponding right-singular matrix. Substituting $V_\Phi$ into Equation (2) and we have:

$$\left[\sqrt{\frac{N-1}{N(N-2)}}(\Phi(x_1)-\tilde{m}_\Phi) \right. \quad (9)$$

$$\left.\sqrt{\frac{1}{N-2}}\Phi(\tilde{X})\right] = \left[\frac{1}{h_\Phi}\sqrt{\frac{N-1}{N(N-2)}}[\Phi(x_1)-\Phi(\tilde{X})B]\Phi(\tilde{X})\tilde{A}\right] \times$$

$$U_\Phi' \Sigma_\Phi' D_\Phi'^T \begin{bmatrix} 1 & 0^T \\ 0_{N-1} & \tilde{D}_\Phi \end{bmatrix}^T =$$

$$\Phi([x_1 \ \tilde{X}])\begin{bmatrix} \frac{1}{h_\Phi}\sqrt{\frac{N-1}{N(N-2)}} & 0^T \\ \frac{1}{h_\Phi}\sqrt{\frac{N-1}{N(N-2)}}B & \tilde{A} \end{bmatrix} \times U_\Phi' \Sigma_\Phi' D_\Phi'^T \begin{bmatrix} 1 & 0^T \\ 0_{N-1} & \tilde{D}_\Phi \end{bmatrix}^T =$$

$$\Phi([\tilde{X} \ x_1])\begin{bmatrix} \tilde{A} & -\frac{1}{h_\Phi}\sqrt{\frac{N-1}{N(N-2)}}B \\ 0^T & \frac{1}{h_\Phi}\sqrt{\frac{N-1}{N(N-2)}} \end{bmatrix} \times$$

$$U_\Phi' \Sigma_\Phi' D_\Phi'^T \begin{bmatrix} 1 & 0^T \\ 0_{N-1} & \tilde{D}_\Phi \end{bmatrix}^T$$

The main factors P of $C^F$ can be expressed as $$P = \Phi([x_1 \ \tilde{X}])\begin{bmatrix} \frac{1}{h_\Phi}\sqrt{\frac{N-1}{N(N-2)}} & 0^T \\ -\frac{1}{h_\Phi}\sqrt{\frac{N-1}{N(N-2)}}B & \tilde{A} \end{bmatrix}U_\Phi' \quad (10)$$

$$= \Phi(X)\begin{bmatrix} \frac{1}{h_\Phi}\sqrt{\frac{N-1}{N(N-2)}} & 0^T \\ -\frac{1}{h_\Phi}\sqrt{\frac{N-1}{N(N-2)}}B & \tilde{A} \end{bmatrix}U_\Phi'$$

And $P = \Phi(X)A$, so we get Equation (11)

$$A = \begin{bmatrix} \frac{1}{h_\Phi}\sqrt{\frac{N-1}{N(N-2)}} & 0^T \\ -\frac{1}{h_\Phi}\sqrt{\frac{N-1}{N(N-2)}}B & \tilde{A} \end{bmatrix}U_\Phi' \quad (11)$$

From Equation (11), $\tilde{A}$ can be calculated:

$$\begin{bmatrix} \frac{1}{h_\Phi}\sqrt{\frac{N-1}{N(N-2)}} & 0^T \\ -\frac{1}{h_\Phi}\sqrt{\frac{N-1}{N(N-2)}} B & \tilde{A} \end{bmatrix} = A(U'_\Phi)^{-1} \quad (5)$$

After the main factors P is obtained from the initial monitoring model of the continuous annealing process in Step 2 and we can get the score vector $t \in R^r$ in the feature space of the continuous annealing process.

$$t = P^T[\Phi(x_{new}) - m_\Phi] \quad (12)$$
$$= A^T \Phi(X)^T \Phi(X)^T \left[\Phi(x_{new}) - \frac{1}{N}\Phi(X)1_N\right]$$
$$= A^T \left[k(X, x_{new}) - \frac{1}{N}K(X)1_N\right]$$

where $P = [p_1, p_2, \ldots, p_r]$, r is the number of the retaining nonlinear principal component, $k(X, x_{new})$ indicates the inner product of the sample matrix X and the new sample $x_{new}$ in the continuous annealing process. $T^2$ and SPE statistics of the new samples $x_{new}$ are calculated by Equation (13) and (14).

$$T_1^2 = t^T \Lambda^{-1} t \quad (13)$$

$$SPE_1 = [\Phi(x_{new}) - m_\Phi]^T (I - PP^T)[\Phi(x_{new}) - m_\Phi] \quad (14)$$

where $\Lambda$ is the eigenvalues matrix of the principal component. $T^2$ statistic satisfies the F distribution:

$$T^2 = \frac{r(N^2 - 1)}{N(N-r)} F_{r, N-r}$$

Among them, N is the number of the sample, r is the number of the retaining principal component, the upper limit of the $T^2$ statistic is $$T_\beta^2 = \frac{r(N^2 - 1)}{N(N-r)} F_{r, N-r, \beta} \quad (15)$$

Among them, $\beta$ is the confidence level, while the Q statistic meets the $\chi^2$ distribution, the control upper limit is $$Q_\beta = g\chi^2(h) \quad (16)$$

Among them, $g = \rho^2/2\mu, h = 2\mu^2/\rho^2$, $\mu$ and $\rho^2$ indicate the sample mean and variance corresponding Q statistic. If $T_1^2$ and $SPE_1$ are greater than their respective confidence, an alarm occurs, which indicates the continuous annealing process anomalies occur. Otherwise go to step 3.

Update the initial monitoring model of the continuous annealing process of step 2 using the recursive kernel principal component analysis stated by step 3, and calculate the main factors $\hat{P}$ after updating the continuous annealing process model. The method is as follows:

$x_{new}$ is a new samples in the continuous annealing process and can be used, $\Phi(x_{new})$ is the new samples $x_{new}$'s projection in the feature space in the continuous annealing process, $\Phi(X_{new}) = \Phi([\tilde{X} \ x_{new}])$ is the samples matrix's projection in the feature space in the updated continuous annealing process, the mean matrix $\hat{m}_\Phi$ of $\Phi(X_{new})$ and covariance matrix $\hat{C}^F$ are respectively $$\hat{m}_\Phi = \frac{1}{N}\Phi([\tilde{X} \ x_{new}])1_N = \frac{N-1}{N}\tilde{m}_\Phi + \frac{1}{N}\Phi(x_{new}) \quad (17)$$

$$\hat{C}^F = \frac{1}{N-1} \overline{\Phi}([\tilde{X} \ x_{new}])\overline{\Phi}([\tilde{X} \ x_{new}])^T \quad (18)$$
$$= \frac{N-2}{N-1}\left[\sqrt{\frac{N-1}{N(N-2)}}(\Phi(x_{new}) - \tilde{m}_\Phi) \sqrt{\frac{1}{N-2}}\overline{\Phi}(\tilde{X})\right] \times$$
$$\left[\sqrt{\frac{N-1}{N(N-2)}}(\Phi(x_{new}) - \tilde{m}_\Phi) \sqrt{\frac{1}{N-2}}\overline{\Phi}(\tilde{X})\right]^T$$

From the equation (2) to (9) we can get $$V'_\Phi = \begin{bmatrix} \sum_\Phi \tilde{A}\tilde{A}^T \sqrt{\frac{N-1}{N(N-2)}} \left(k(\tilde{X}, x_{new}) - \frac{1}{N-1}K(\tilde{X})1_{N-1}\right) \\ 0^T & h'_\Phi \end{bmatrix}$$

We can get $V_\Phi' = U_\Phi'' \Sigma_\Phi'' D_\Phi''^T$ by singular value decomposition of $v_\Phi'$.

And thus we can get the main factors $\hat{P}$ and the engenvalues matrix $\hat{\Lambda}$ of $\hat{C}^F$ $$\hat{P} = \Phi([\tilde{X} \ x_{new}]) \begin{bmatrix} \tilde{A} & -\frac{1}{h'_\Phi}\sqrt{\frac{N-1}{N(N-2)}} B' \\ 0^T & \frac{1}{h'_\Phi}\sqrt{\frac{N-1}{N(N-2)}} \end{bmatrix} U''_\Phi = \Phi(X_{new})\hat{A} \quad (19)$$

$$\hat{\Lambda} = \frac{N-2}{N-1} \Sigma_\Phi''^2 \quad (20)$$

where the regulating factor of the main factors for the updating monitoring model in the continuous annealing process:

$$h'_\Phi = \frac{N-1}{N(N-2)} \sqrt{1 - 2B'^T k(\tilde{X}, x_{new}) + B'^T K(\tilde{X}) B'} \quad (21)$$

The correcting matrix of the main factors for the updating monitoring model in the continuous annealing process:

$$B' = \frac{1}{N-1} 1_{N-1} + \tilde{A}\tilde{A}^T\left(k(\tilde{X}, x_{new}) - \frac{1}{N-1}K(\tilde{X})1_{N-1}\right) \quad (22)$$

$k(\overline{X}, x_{new})$ indicates the inner product of the middle matrix $\overline{X}$ and the new sample $x_{new}$;

By using Hotelling's $T^2$ statistic and squared prediction error (SPE) statistic for fault monitoring stated in step 4, the determining methods of $T^2$ and squared prediction error (SPE) statistics are as follows:

For a new sample z in the continuous annealing process, its score vector $t \in R^r$ in the feature space is $$t = \hat{P}^T[\Phi(z) - \hat{m}_\Phi] \quad (23)$$

$$= \hat{A}^T \Phi(X_{new})^T \left[\Phi(z) - \frac{1}{N}\Phi(X_{new})1_N\right]$$

$$= \hat{A}^T \left[k(X_{new}, z) - \frac{1}{N}K(X_{new})1_N\right]$$

Among them, $\hat{P}=[\hat{p}_1, \hat{p}_2, \ldots, \hat{p}_r]$, r is the number of the retaining principal component, $k(X_{new}, z)$ indicates the inner product vector of the updating samples matrix $X_{new}$ and the new samples $X_{new}$ in the continuous annealing process. $T_2^2$ and $SPE_2$ statistics of the new sample z in the continuous annealing process are calculated from the equation (24) and (25).

$$T_2^2 = t^T \hat{\Lambda}^{-1} t \quad (24)$$

$$SPE_2 = [\Phi(z)-\hat{m}_\Phi]^T (I-\hat{P}\hat{P}^T)[\Phi(z)-\hat{m}_\Phi] \quad (25)$$

where $\hat{\Lambda}$ is the variance matrix of the principal component; The confidence limits of $T_2^2$ and $SPE_2$ statistics of the new sample z can be obtained by the equation (15) and (16). If $T_2^2$ or $SPE_2$ statistics are greater than their confidence limits, we think there is a fault and an alarm will occur. Otherwise go to step 3;

Advantages of the invention: the invention proposes a fault detection method of the continuous annealing process based on the recursive kernel principal component analysis mainly to solve the nonlinear and time-varying data problem. RKPCA updates the model by recursively computing the eigenvalues and main factors of training data covariance. The process monitoring results by using the method shows that the method can not only greatly reduce false alarms, but also improve the accuracy of the fault detection.

DETAILED DESCRIPTION OF THE PREFERRED EMBODIMENT

We illustrate further in detail combining of the following drawings and examples for the invention.

Figure 1:
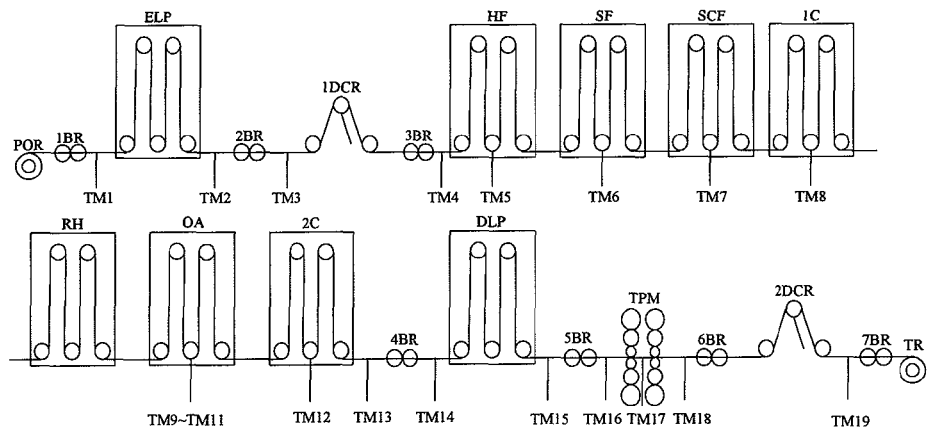
FIG. 1 shows a Physical layout of the continuous annealing process of a fault detection method based on the recursive kernel principal component analysis according to the present invention.

The physical layout of the continuous annealing process is shown in FIG. 1. Where the width of the strip is 900-1230 mm, the thickness is 0.18-0.55 mm, the maximum line speed is 880 m/min, the maximum weight is 26.5 t and is heated to 710° C. The first entry coil is opened by payoff reel (POR), and it is welded into a strip finally. The strip passes through 1# bridle roll (1BR), entry loop (ELP), 2# bridle roll (2BR), 1# dancer roll (1DCR), and 3# bridle roll (3BR), then it enters the continuous annealing furnace. The annealing technologies consist of: rapid cooling-reheating-inclined over ageing. The annealing equipments include heating furnace (HF), soaking furnace (SF), slow cooling furnace (SCF), 1# cooling furnace (1C), reheating furnace (RF), over ageing furnace (OA), and 2# cooling furnace (2C). After completing the annealing craft, the strip in turn pass through 4# bridle roll (4BR), delivery loop (DLP), and 5# bridle roll (5BR), and temper rolling machine (TPM), 6# bridle roll (6BR), 2# dancer roll (2DCR), and 7# bridle roll (7BR). Finally, the strip enters roll type reel (TR) to become coil.

Figure 2:
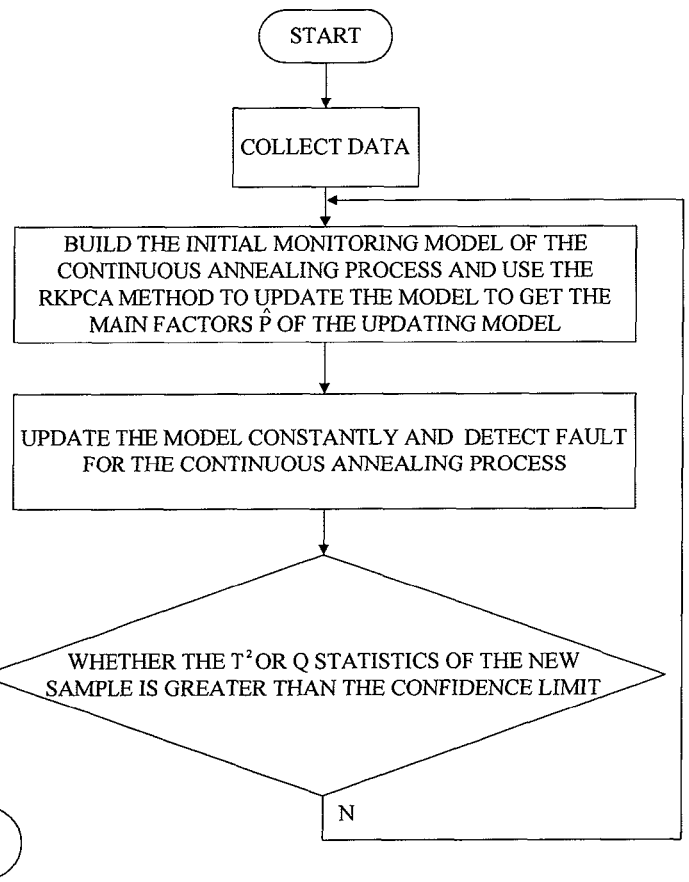
FIG. 2 shows a total flow figure of the fault detection method in the continuous annealing process based on the recursive kernel principal component analysis in the invention.
Figure 3:
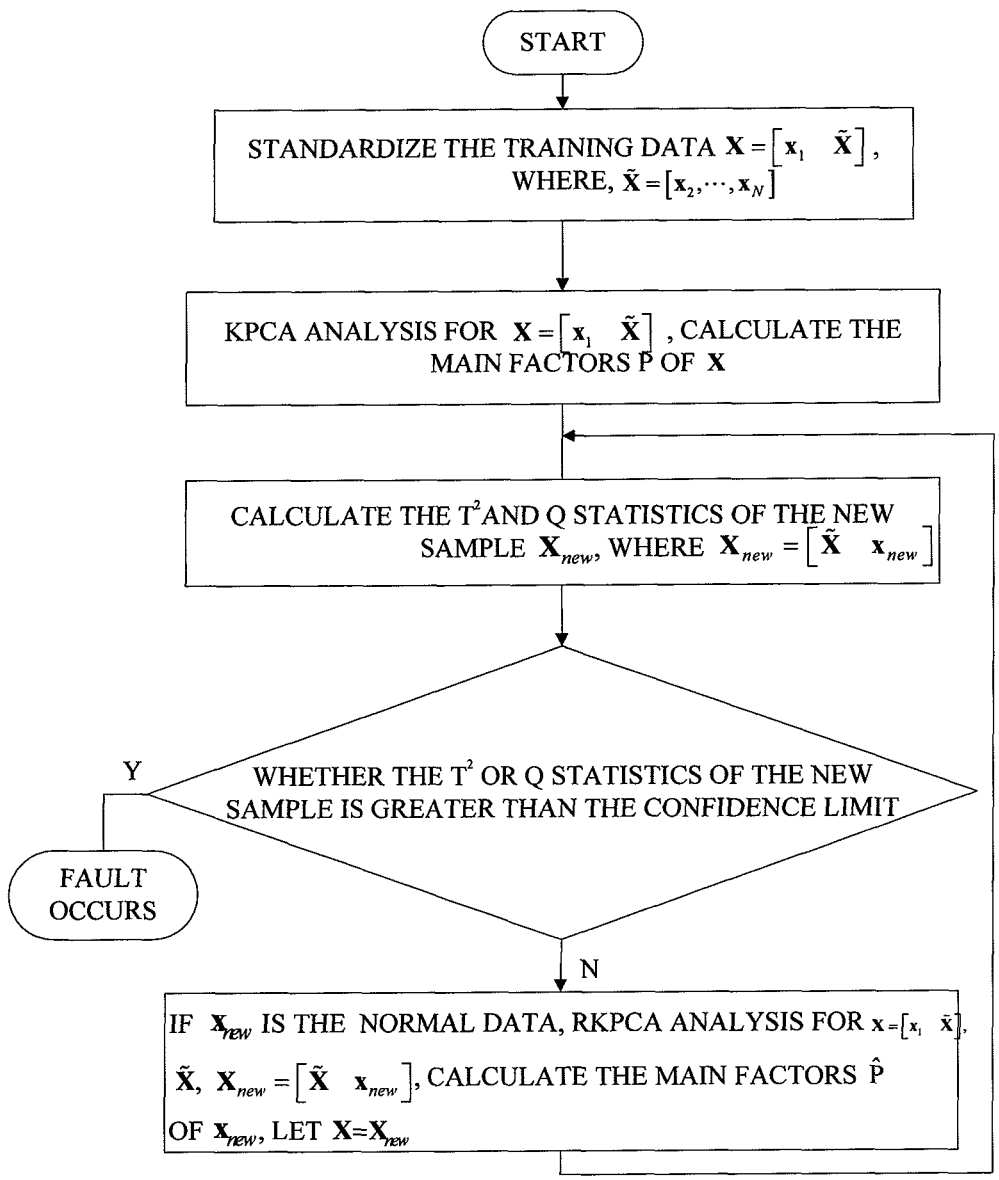
FIG. 3 shows a model flow picture in the continuous annealing process based on the recursive kernel principal component analysis in the invention.

The invention is the fault detection method of the continuous annealing process based on the recursive kernel principal component analysis, shown in FIG. 2, including the following steps:

Step 1: Collect data and standardize the collecting data, collecting data in the continuous annealing industrial process including: the roll speed, current and tension of entry loop (ELP), which includes 37 roll speed variables, 37 current variables, and 2 tension variable in both sides of ELP;

There are a total of 76 process variables of ELP in the continuous annealing process. There are 200 history samples. Also, there are 300 real time samples. 99% confidence limits are selected. Each sample contains 76 variables. Some sample data are shown in Table 1 and Table 2, and ten sets of data randomly selected from the training data and test data is shown in Table 1 and Table 2.

TABLE 1

Ten sets of the history data of ELP

| | | | | Var. | | | | |
|---|---|---|---|---|---|---|---|---|
| No. | 1R Current | 1R Roller Speed | 5R Current | 5R Roller Speed | 18R Current | 18R Roller Speed | TM1 Tension | TM2 Tension |
| 1 | 0.658610 | 36.4698 | 38.2673 | 747.034 | 31.0010 | 657.585 | 6.73518 | 6.70954 |
| 2 | 0.663005 | 36.6896 | 37.6600 | 746.140 | 31.4893 | 658.350 | 6.66926 | 6.85237 |
| 3 | 0.670451 | 36.5461 | 35.5238 | 746.864 | 30.0122 | 657.606 | 6.74617 | 6.69856 |
| 4 | 0.670451 | 36.1189 | 39.4514 | 746.736 | 30.3754 | 658.159 | 7.10506 | 6.92927 |
| 5 | 0.663493 | 36.2135 | 36.8147 | 746.715 | 29.6674 | 657.861 | 6.65827 | 6.51179 |
| 6 | 0.664347 | 36.4179 | 36.1402 | 747.034 | 30.7416 | 657.904 | 6.43854 | 6.73518 |
| 7 | 0.664958 | 36.2196 | 38.4047 | 746.396 | 31.1139 | 657.734 | 6.52277 | 6.39826 |

TABLE 1-continued

Ten sets of the history data of ELP

| | | | | Var. | | | | |
|---|---|---|---|---|---|---|---|---|
| No. | 1R Current | 1R Roller Speed | 5R Current | 5R Roller Speed | 18R Current | 18R Roller Speed | TM1 Tension | TM2 Tension |
| 8 | 0.659953 | 36.1097 | 37.1046 | 746.587 | 30.7691 | 658.159 | 6.45319 | 6.62898 |
| 9 | 0.662028 | 36.4332 | 36.3661 | 746.162 | 30.5676 | 658.201 | 6.56306 | 6.39826 |
| 10 | 0.664225 | 36.1921 | 37.9866 | 746.672 | 30.7416 | 657.670 | 6.88167 | 6.53376 |

TABLE 2

Ten sets of the real time data of ELP a

| | | | | Var. | | | | |
|---|---|---|---|---|---|---|---|---|
| No. | 1R Current | 1R Roller Speed | 5R Current | 5R Roller Speed | 18R Current | 18R Roller Speed | TM1 Tension | TM2 Tension |
| 1 | 0.656535 | 35.7221 | 37.8920 | 745.694 | 29.9603 | 657.797 | 6.37263 | 6.81941 |
| 2 | 0.624918 | 35.4292 | 37.9347 | 736.379 | 25.1995 | 650.845 | 6.69490 | 6.61433 |
| 3 | 0.631876 | 34.9012 | 41.1604 | 726.468 | 27.5799 | 640.448 | 6.48249 | 7.02815 |
| 4 | 0.683879 | 34.5380 | 46.0769 | 720.811 | 31.4801 | 631.986 | 6.30304 | 6.79377 |
| 5 | 0.649088 | 34.2237 | 46.5621 | 718.833 | 34.0131 | 631.178 | 6.24811 | 7.06111 |
| 6 | 0.686442 | 34.2542 | 50.6851 | 715.600 | 35.4231 | 626.947 | 6.32135 | 6.72786 |
| 7 | 0.688273 | 34.0864 | 51.7044 | 716.174 | 35.5421 | 627.351 | 6.39094 | 6.86336 |
| 8 | 0.687419 | 34.1535 | 52.4125 | 715.919 | 33.1891 | 627.372 | 6.66926 | 6.72053 |
| 9 | 0.690959 | 34.2634 | 53.9841 | 715.898 | 33.0396 | 627.159 | 6.44587 | 6.63264 |
| 10 | 0.700481 | 34.2359 | 55.3880 | 715.515 | 32.2095 | 627.308 | 6.50080 | 6.77546 |

Step 2: Build the initial monitoring model of ELP in the continuous annealing process and calculate the main factor P of fault in the continuous annealing process and determine confidence limits by using 200 samples after standardized samples in Step 1. Monitor a new sample $x_{new}$ of continuous annealing process. If it is abnormal, an alarm will be given, otherwise go to Step 3.

Set 200 samples of the continuous annealing process as the matrix X, and the latter 199 data of the samples as the mediate matrix $\tilde{X}$. They are mapped to high dimensional feature space by the projection $\Phi$; Find the transmission factor $\tilde{A}$ of the middle matrix, according to equations (2) and (10), we can get the covariance matrix $C^F$ and the main factor P of the sample matrix X by calculating and the $T_1^2$ and SPE, statistics of the new sample $x_{new}$ in continuous annealing process using the main factors P according to equations (13) and (14) and determine whether they are greater their respective confidence limit. There is no fault by calculating and go to step 3.

Step 3: Use recursive kernel principal component analysis method to update the initial monitoring model of continuous annealing process in Step 2 and calculate the main factor $\hat{P}$ of fault in the continuous annealing process after updating continuous annealing model according to Equation (19);

$x_{new}$ is a new sample of the continuous annealing process, $\Phi(x_{new})$ is the mapping to the feature space of the new sample $x_{new}$ of the continuous annealing process. $\Phi(X_{new})=\Phi([\tilde{X}\ x_{new}])$ is the updating sample matrix of the continuous annealing process and the transmission factor $\hat{A}$ and eigenvalues matrix $\hat{A}$ of the updated covariance $\hat{C}^F$ can be calculated by equations (19) and (20), respectively. Thus we can get the main factor $\hat{P}$ of the updating sample matrix in the continuous annealing process. Here we randomly select ten sets of data of the transmission factor, as shown in Table 3.

TABLE 3

Ten sets of data of the transmission factor $\hat{A}$

| | | | | | | | |
|---|---|---|---|---|---|---|---|
| −0.002234 | 0.116932 | 0.02946 | 0.004251 | −0.031282 | 0.00692 | −0.14756 | −0.000921 |
| 0.0202367 | −0.00366 | 0.00288 | −0.00933 | 0.0136258 | 0.06262 | 0.073793 | −0.040450 |
| 0.0326804 | −0.05354 | −0.0026 | 0.009399 | 0.0695079 | 0.09472 | 0.082283 | −0.057724 |
| −0.025156 | −0.00394 | 0.06529 | 0.056101 | 0.0082486 | −0.0995 | −0.16148 | −0.014453 |
| 0.0546749 | −0.01765 | −0.0377 | −0.04835 | 0.0261276 | 0.05037 | 0.033161 | 0.0056228 |
| 0.0020289 | 0.04197 | 0.01145 | −0.02075 | −0.075466 | −0.1277 | −0.15009 | 0.0565441 |
| 0.0031576 | −0.12491 | −0.0031 | 0.029215 | 0.1613627 | 0.09810 | 0.067874 | −0.1144526 |
| 0.0374927 | −0.01329 | 0.03562 | −0.00175 | −0.031035 | −0.09767 | −0.10696 | 0.0197142 |
| 0.0436574 | −0.07263 | 0.01474 | −1.80547 | 0.098647 | 0.038714 | −0.01312 | −0.0633847 |
| 0.0876383 | 0.048630 | −0.01972 | −0.10252 | −0.01356 | 0.028529 | −0.06496 | −0.0162924 |

Step 4: Fault Detection by Using the Updated Continuous Annealing Process Model;

By using Hotelling's $T^2$ statistic and squared prediction error (SPE) statistic for fault detection, we can determine whether the fault of the continuous annealing process occurs. When the $T^2$ statistic or SPE statistic are beyond their respective confidence limit, we think that there is a fault; otherwise the whole process is normal and goes to Step 3 and continues to update the monitoring model.

Figure 4:
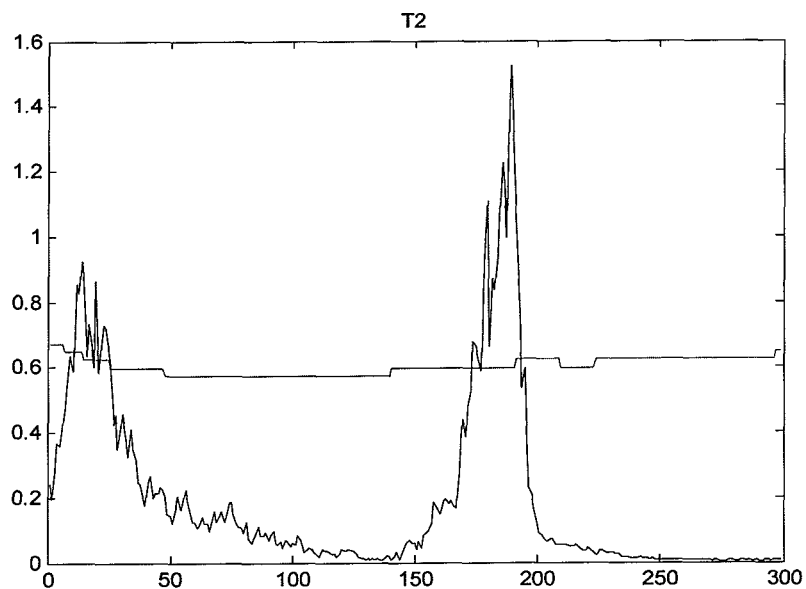
FIG. 4 shows the $T^2$ statistic of the fault detection method in the continuous annealing process based on the recursive kernel principal component analysis in the invention.
Figure 5:
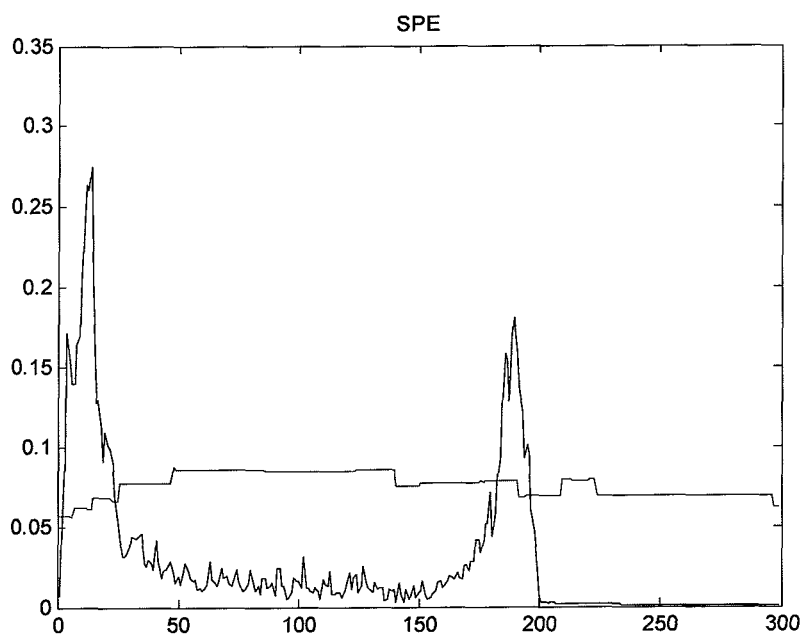
FIG. 5 shows the SPE statistic of the fault detection method in the continuous annealing process based on the recursive kernel principal component analysis in the invention.
Figure 6:
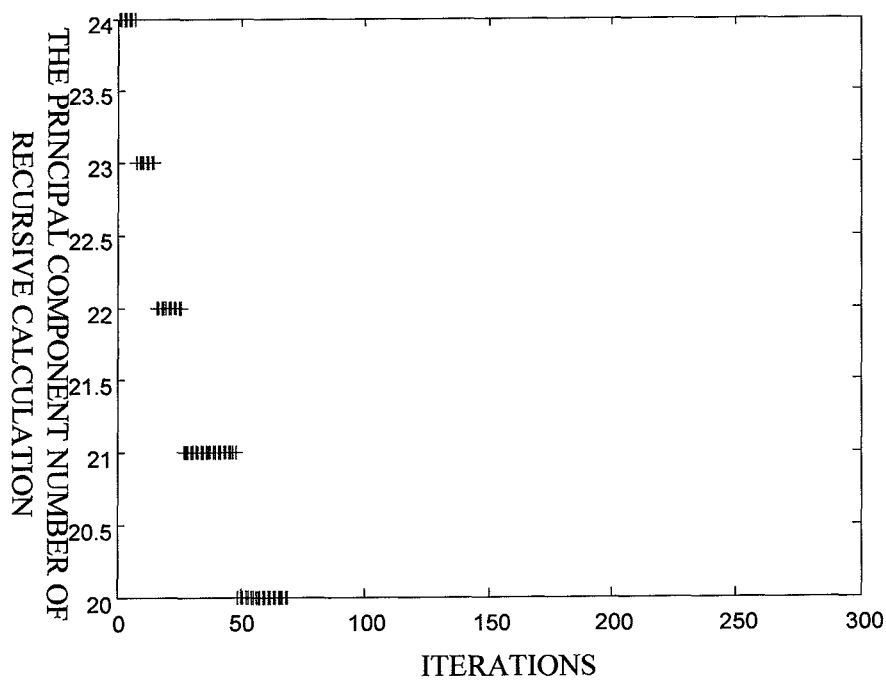
FIG. 6 shows the number of the calculated principal component in the fault detection method in the continuous annealing process based on the recursive kernel principal component analysis in the invention.
Figure 7:
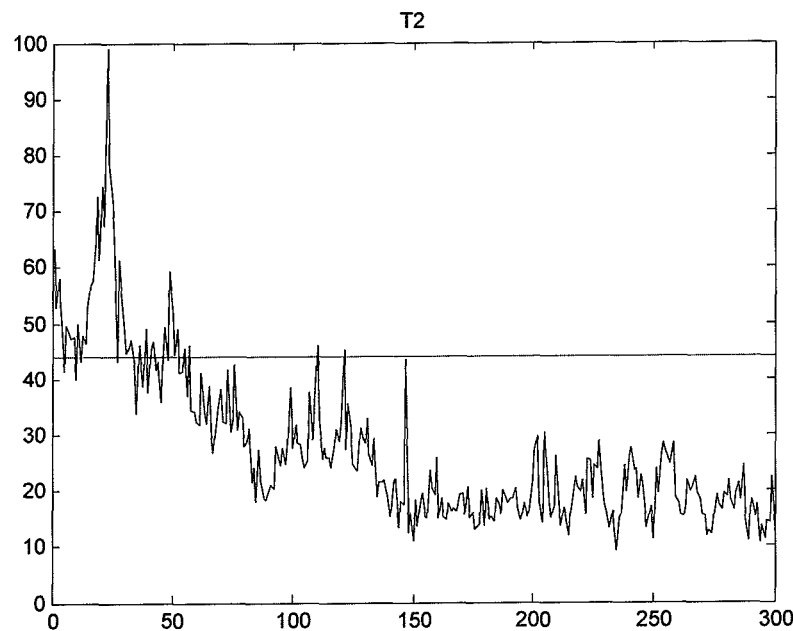
FIG. 7 shows the $T^2$ statistic of the fault detection method in the continuous annealing process based on the recursive kernel principal component analysis in the invention.
Figure 8:
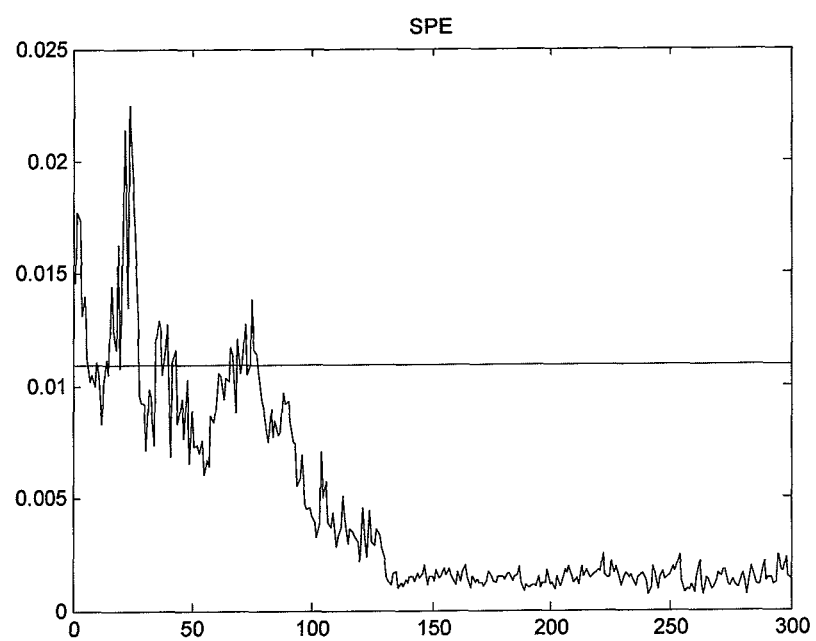
FIG. 8 shows the SPE statistic of the fault detection method in the continuous annealing process based on the recursive kernel principal component analysis in the invention.

RKPCA uses 200 history samples of the continuous annealing process to build the initial model and then we can update the model according to 300 real time data. We use the $T^2$ and SPE statistics in order to monitor the process. For a new sample z among 300 real time data, its score vector t in the feature space can be computed by Equation (23). The $T^2$ and SPE statistics of the new sample z are calculated by Equation (24) and (25), and then we can determine their confidence limits according to Equation (15) and (16). When the $T^2$ statistic and SPE statistic are greater than their confidence limit we think that there is failure and an alarm is given. On the contrary, the whole process is normal. Go to step 3 and continue to update the monitoring model. The monitoring results for the continuous annealing process by calculating are shown in FIG. 4 and FIG. 5. We can see that the $T^2$ and SPE statistics generated by RKPCA method exceed the confidence limit at sample 175. In fact, the beak strip fault is introduced at sample 175. The simulation results shows that the proposed RKPCA method by updating recursively the model ensure that the model's effectiveness in the process of change so that we can monitor timely the continuous annealing process failure. FIG. 4 and FIG. 5 shows that the confidence limit based on the RKPCA method has also been updated. FIG. 6 shows the changes of the number of the retained principal component. On the contrast, when KPCA method is used to monitor the continuous annealing process, the model can't be updated recursively. The generated $T^2$ and SPE statistics are shown in FIGS. 7 and 8. In the first stage, due to the continuous annealing process's instability, the $T^2$ and SPE statistics exceed temporarily their respective confidence limits, but in the stable process, there is no fault.

The above simulation example shows in the invention—the effectiveness of the fault detection in the continuous annealing process based on the recursive kernel principal component analysis and realizes monitoring of the continuous annealing process.

What is claimed is:

1. A fault detection method in a continuous annealing process based on a recursive kernel principal component analysis (RKPCA), comprising the following steps:

Step 1: collecting data and standardizing samples using a processor by detecting roll speed, current and tension of an entry loop (ELP);

Step 2: extracting principal factors P of the fault in the continuous annealing process using the processor by building an initial monitoring model of the continuous annealing process with N standardized samples in Step 1; monitoring a new sample $x_{new}$ of the continuous annealing process, and if it is abnormal, generating an alarm, otherwise going to Step 3; wherein the extracted principal factor P in the continuous annealing process is as follows:

$$P = \Phi(X) \begin{bmatrix} \frac{1}{h_\Phi}\sqrt{\frac{N-1}{N(N-2)}} & 0^T \\ -\frac{1}{h_\Phi}\sqrt{\frac{N-1}{N(N-2)}} B & \tilde{A} \end{bmatrix} U'_\Phi$$

where $\Phi(X)$ is a mapping matrix of N samples $X=[x_1, x_2, \ldots, x_N]$, N is a sample number, the regulating factor of the initial monitoring model in the continuous annealing process is $$h_\Phi = \frac{N-1}{N(N-2)}\sqrt{1 - 2B^T k(X, x_1) + B^T K(X)B},$$

the correcting matrix of the initial monitoring model in the continuous annealing process is $$B = \frac{1}{N-1}1_{N-1} + \tilde{A}\tilde{\Lambda}\tilde{A}^T\left(k(\tilde{X}, x_1) - \frac{1}{N-1}K(\tilde{X})1_{N-1}\right),$$

$k(X,x_1)$ indicates the inner product of x and $x_1$, $K(X)$ indicates the inner product of the sample matrix, $k(\tilde{X},x_1)$ is the inner product of $\tilde{X}$ and $x_1$, $\tilde{X}$ is the middle matrix, $K(\tilde{X})$ indicates the inner product of the middle matrix, $\tilde{\Lambda}$ is the eigenvalues matrix of the middle matrix covariance, $U'_\Phi$ is the eigenvectors matrix of the process variables, $1_{N-1}$ is the unit vector in N−1 column;

Extracting the transmission factor of the continuous annealing process, which is expressed as $$\begin{bmatrix} \frac{1}{h_\Phi}\sqrt{\frac{N-1}{N(N-2)}} & 0^T \\ -\frac{1}{h_\Phi}\sqrt{\frac{N-1}{N(N-2)}} B & \tilde{A} \end{bmatrix} = A(U'_\Phi)^{-1}$$

the Step 3: when the continuous annealing process sample $x_{new}$ is normal data, updating, using the processor, the initial monitoring model of the continuous annealing process built in the Step 2 and calculating the principal factor $\hat{P}$ of the fault in the updated continuous annealing process model by using the RKPCA, in which $\hat{P}$ is expressed as follows:

$$\hat{P} = \Phi([\tilde{X}\ x_{new}])\begin{bmatrix} \tilde{A} & -\frac{1}{h'_\Phi}\sqrt{\frac{N-1}{N(N-2)}} B' \\ 0^T & \frac{1}{h'_\Phi}\sqrt{\frac{N-1}{N(N-2)}} \end{bmatrix} U''_\Phi = \Phi(X_{new})\hat{A}$$

where $\Phi(X_{new})=\Phi([\tilde{X}\ x_{new}])$ is the updated mapping matrix, the regulating factor of the updated monitoring model in the continuous annealing process is $$h'_\Phi = \frac{N-1}{N(N-2)}\sqrt{1 - 2B'^T k(\tilde{X}, x_{new}) + B'^T K(\tilde{X})B'},$$

the regulating matrix of the updating monitoring model in the continuous annealing process is $$B' = \frac{1}{N-1}1_{N-1} + \tilde{A}\tilde{\Lambda}\tilde{A}^T\left(k(\tilde{X}, x_{new}) - \frac{1}{N-1}K(\tilde{X})1_{N-1}\right),$$

$k(\tilde{X}, x_{new})$ indicates the inner product of $\tilde{X}$ and $x_{new}$;

Step 4: detecting, using the processor, the fault for the continuous annealing process;

wherein the fault of the continuous annealing process can be judged by using Hotelling's $T^2$ statistic and squared prediction error (SPE) statistic, when the $T^2$ statistic and SPE statistic exceed their confidence limit, a failure is identified; on the contrary, the whole process is normal, go to the step 3 to continue to update the initial monitoring model of the continuous annealing process, and outputting the identified failure.

2. The method as claimed in claim 1, wherein the Step 2 of building the initial monitoring model of the continuous annealing process in the Step 1 includes the following steps:

updating, using the processor, recursively eigenvalues in the feature space of the sample covariance matrix by the RKPCA;

letting, using the processor, $X=[x_1, x_2, \ldots, x_N]$ be the sample matrix of the continuous annealing process, wherein $x_1, x_2, \ldots, x_N$ are the samples of the continuous annealing process, N is the sample number, $\tilde{X}=[x_2, \ldots, x_N] \in R^{m \times (N-1)}$ is the middle matrix of the continuous annealing process, m is the number of sampling variables in the continuous annealing process, $X_{new}[\tilde{X}\,x_{new}]$ is the sample matrix of updating model in the continuous annealing process, $x_{new}$ is the new sample of the continuous annealing process; mapping $X$, $\tilde{X}$ and $X_{new}$ to the high-dimensional feature space to become $\Phi(X)$, $\Phi(\tilde{X})$ and $\Phi(X_{new})$, respectively, so the mean vector $m_\Phi$ and covariance matrix $C^F$ of $\Phi(X)$ can be calculated $$m_\Phi = \frac{1}{N}\Phi([x_1 \ \tilde{X}])1_N = \frac{1}{N}\Phi(x_1) + \frac{N-1}{N}\tilde{m}_\Phi \quad \text{Equation (1)}$$

$$C^F = \frac{1}{N-1}\Phi([x_1 \ \tilde{X}])\Phi([x_1 \ \tilde{X}])^T =$$

$$\frac{1}{N-1}(\Phi(x_1)-m_\Phi)(\Phi(x_1)-m_\Phi)^T +$$

$$\frac{1}{N-1}\sum_{i=2}^{N}(\Phi(x_i)-m_\Phi)(\Phi(x_i)-m_\Phi)^T =$$

$$\frac{1}{N-1}\left[\frac{N-1}{N}\Phi(x_1)-\frac{N-1}{N}\tilde{m}_\Phi\right]\left[\frac{N-1}{N}\Phi(x_1)-\frac{N-1}{N}\tilde{m}_\Phi\right]^T \quad \text{Equation (2)}$$

-continued $$+\frac{1}{N-1}\sum_{i=2}^{N}\left[\Phi(x_i)-\tilde{m}_\Phi+\frac{1}{N}\tilde{m}_\Phi-\frac{1}{N}\Phi(x_1)\right] \times \left[\Phi(x_i)-\tilde{m}_\Phi+\frac{1}{N}\tilde{m}_\Phi-\frac{1}{N}\Phi(x_1)\right]^T =$$

$$\frac{1}{N}(\Phi(x_1)-\tilde{m}_\Phi)(\Phi(x_1)-\tilde{m}_\Phi)^T +$$

-continued $$\frac{1}{N-1}\sum_{i=2}^{N}(\Phi(x_i)-\tilde{m}_\Phi)(\Phi(x_i)-\tilde{m}_\Phi)^T =$$

$$\frac{1}{N}(\Phi(x_1)-\tilde{m}_\Phi)(\Phi(x_1)-\tilde{m}_\Phi)^T + \frac{N-2}{N-1}\tilde{C}^F =$$

$$\frac{N-2}{N-1}\left[\sqrt{\frac{N-1}{N(N-2)}}(\Phi(x_1)-\tilde{m}_\Phi) \quad \sqrt{\frac{1}{N-2}}\Phi(\tilde{X})\right] \times$$

$$\left[\sqrt{\frac{N-1}{N(N-2)}}(\Phi(x_1)-\tilde{m}_\Phi) \quad \sqrt{\frac{1}{N-2}}\Phi(\tilde{X})\right]^T$$

wherein $\tilde{m}_\Phi$ and $\tilde{C}_F$ represent the mean vector and covariance matrix of $\Phi(\tilde{X})$, respectively, $\overline{\Phi}([x_1 \ \tilde{X}])$ is the mean matrix of $\Phi(X)$, $1_N$ is a row vector consisting of 1 with the number of N, $\Phi(x_i)$ is the mapping vector to the high-dimensional feature space of $x_i$, i=1 ... N, $\overline{\Phi}(\tilde{X})$ is the mean matrix of $\Phi(\tilde{X})$;

letting, using the processor, $\Lambda$ and $P$ be the eigenvalues matrix and the main factors of $C^F$, respectively, $\tilde{\Lambda}$ and $\tilde{P}$ be the eigenvalues matrix and the main factors of covariance matrix $\tilde{C}^F$ of $\Phi(\tilde{X})$, respectively, wherein assume $\tilde{P}=PR_\Phi$, $R_\Phi$ is an orthogonal rotation matrix, due to $P=\Phi(X)A$, $\tilde{P}=\Phi(\tilde{X})\tilde{A}$, where $A=(I-(1/N)\times E_N)[v_1/\sqrt{\xi_1}, v_2/\sqrt{\xi_2}, \ldots, v_i/\sqrt{\xi_i}]$, $\xi_i$ and $v_i$ indicate the ith eigenvalues and eigenvectors of $\overline{\Phi}(\tilde{X})^T\overline{\Phi}(\tilde{X})$, respectively, $\tilde{A}=(I-(1/(N-1))\times E_{N-1})[\tilde{v}_1/\sqrt{\omega_1}, \tilde{v}_2/\sqrt{\omega_2}, \ldots, \tilde{v}_i/\sqrt{\omega_i}]$, $\omega_i$ and $\tilde{v}_i$ indicate the ith eigenvalues and eigenvectors of $\overline{\Phi}(\tilde{X})^T\overline{\Phi}(\tilde{X})$, $P^TC^FP=\Lambda$ and $\tilde{P}^T\tilde{C}^F\tilde{P}=\tilde{\Lambda}$ can be obtained by diagonalizing $C^F$ and $\tilde{C}^F$, respectively, $[(N-1)/(N-2)]\Lambda-[(N-1)/(N(N-2))]g_\Phi g_\Phi^T=R_\Phi\tilde{\Lambda}R_\Phi^T$ can be obtained by calculating the Equation (2), wherein $g_\Phi=P^T(\Phi(x_1)-\tilde{m}_\Phi)=A^T[k(X,x_1)-(1/(N-1))K(X,\tilde{X})1_{N-1}]$;

letting, using the processor, $S_\Phi=[(N-1)/(N-2)]\Lambda-[(N-1)/(N(N-2))]g_\Phi g_\Phi^T$, $\tilde{\Lambda}$ and $R_\Phi$ are the eigenvalues matrix and eigenvectors matrix of $S_\Phi$, Equation (3) can be obtained from Equation (2)

$$P^TC^FP = \frac{1}{N}P^T(\Phi(x_1)-\tilde{m}_\Phi)(\Phi(x_1)-\tilde{m}_\Phi)^TP + \frac{N-2}{N-1}P^T\tilde{C}^FP \quad \text{the Equation (3)}$$

$$= \frac{1}{N}g_\Phi g_\Phi^T + \frac{N-2}{N-1}A^T\Phi(X)^T\tilde{P}\tilde{\Lambda}\tilde{P}^T\Phi(X)A$$

$$= \frac{1}{N}g_\Phi g_\Phi^T + \frac{N-2}{N-1}A^T\Phi(X)^T\Phi(\tilde{X})\tilde{A}\tilde{\Lambda}\tilde{A}^T\Phi(\tilde{X})^T\Phi(X)A$$

$$= \frac{1}{N}g_\Phi g_\Phi^T + \frac{N-2}{N-1}A^TK(X,\tilde{X})\tilde{A}\tilde{\Lambda}\tilde{A}^TK(X,\tilde{X})^TA$$

$$= \Lambda$$

where $K(X,\tilde{X})$ indicates the inner product of sample matrix and middle matrix in the continuous annealing process;

where the singular value decomposition in Equation (2) satisfies:

$$\sqrt{\frac{1}{N-2}}\Phi(\tilde{X}) = \tilde{P}\tilde{\Sigma}_\Phi\tilde{D}_\Phi^T \quad \text{Equation (4)}$$

where $\tilde{P}=\Phi(\tilde{X})\tilde{A}$ is the main factor of $\tilde{C}^F$, $\tilde{\Sigma}_\Phi$ is the diagonal matrix and satisfies $\tilde{\Sigma}_\Phi^2=\tilde{\Lambda}$, $\tilde{D}_\Phi$ is the corresponding right-singular matrix; from the Equations (4) and (2), $$\left[\sqrt{\frac{N-1}{N(N-2)}}(\Phi(x_1)-\tilde{m}_\Phi) \quad \sqrt{\frac{1}{N-2}}\bar{\Phi}(\tilde{X})\right]= \qquad \text{Equation (5)}$$

$$[u_\Phi \quad \tilde{P}]\begin{bmatrix} h_\Phi & 0^T \\ \tilde{\Lambda}\tilde{P}^T\sqrt{\frac{N-1}{N(N-2)}}(\Phi(x_1)-\tilde{m}_\Phi) & \tilde{\Sigma}_\Phi \end{bmatrix}\begin{bmatrix} 1 & 0^T \\ 0_{N-1} & \tilde{D}_\Phi \end{bmatrix}^T$$

$$=$$

$$[u_\Phi \quad \tilde{P}]\begin{bmatrix} h_\Phi & 0^T \\ \tilde{\Lambda}R_\Phi^T\tilde{P}^T\sqrt{\frac{N-1}{N(N-2)}}(\Phi(x_1)-\tilde{m}_\Phi) & \tilde{\Sigma}_\Phi \end{bmatrix}\begin{bmatrix} 1 & 0^T \\ 0_{N-1} & \tilde{D}_\Phi \end{bmatrix}^T$$

where the regulating factor of the initial monitoring model in the continuous annealing process:

$$h_\Phi = \left\|(I-\tilde{P}\tilde{\Lambda}\tilde{P}^T)\sqrt{\frac{N-1}{N(N-2)}}(\Phi(x_1)-\tilde{m}_\Phi)\right\|$$

$$= \sqrt{\frac{N-1}{N(N-2)}}\left\|(I-\tilde{P}\tilde{\Lambda}\tilde{P}^T)(\Phi(x_1)-\tilde{m}_\Phi)\right\|$$

$$= \sqrt{\frac{N-1}{N(N-2)}}\left\|\Phi(x_1)-\frac{1}{N-1}\Phi(\tilde{X})1_{N-1}-\Phi(\tilde{X})\tilde{A}\tilde{\Lambda}\tilde{A}^T\left(\Phi(\tilde{X})^T\Phi(x_1)-\frac{1}{N-1}\Phi(\tilde{X})^T\Phi(\tilde{X})1_{N-1}\right)\right\|$$

$$= \frac{N-1}{N(N-2)}\left\|\Phi(x_1)-\frac{1}{N-1}\Phi(\tilde{X})1_{N-1}-\Phi(\tilde{X})\tilde{A}\tilde{\Lambda}\tilde{A}^T\left(k(\tilde{X},x_1)-\frac{1}{N-1}K(\tilde{X})1_{N-1}\right)\right\|$$

$$= \frac{N-1}{N(N-2)}\left\|\Phi(x_1)-\Phi(\tilde{X})B\right\|$$

$$= \frac{N-1}{N(N-2)}\sqrt{1-2B^Tk(\tilde{X},x_1)+B^TK(\tilde{X})B}$$

$$u_\Phi = \frac{1}{h_\Phi}\sqrt{\frac{N-1}{N(N-2)}}(I-\tilde{P}\tilde{\Lambda}\tilde{P}^T)(\Phi(x_1)-\tilde{m}_\Phi) \qquad \text{Equation (7)}$$

$$= \frac{1}{h_\Phi}\sqrt{\frac{N-1}{N(N-2)}}[\Phi(x_1)-\Phi(\tilde{X})B]$$

where the correcting matrix of the main factors for the initial model in the continuous annealing process:

$$B = \frac{1}{N-1}1_{N-1}+\tilde{A}\tilde{\Lambda}\tilde{A}^T\left(k(\tilde{X},x_1)-\frac{1}{N-1}K(\tilde{X})1_{N-1}\right) \qquad \text{Equation (8)}$$

where $K(\tilde{X})$ indicates the inner product of the middle matrix in the continuous annealing process, $k(\tilde{X},x_1)$ indicates the inner product of $\tilde{X}$ and $x_1$;

setting, using the processor, $$V_\Phi = \begin{bmatrix} h_\Phi & 0^T \\ \tilde{\Lambda}R_\Phi^T\tilde{P}^T\sqrt{\frac{N-1}{N(N-2)}}(\Phi(x_1)-\tilde{m}_\Phi) & \tilde{\Sigma}_\Phi \end{bmatrix}$$

$$= \begin{bmatrix} h_\Phi & 0^T \\ \tilde{\Lambda}R_\Phi^T\tilde{A}^T\sqrt{\frac{N-1}{N(N-2)}}\left(k(X,x_1)-\frac{1}{N-1}K(X,\tilde{X})1_{N-1}\right) & \tilde{\Sigma}_\Phi \end{bmatrix}$$

obtaining, using the processor, $V_\Phi=U_\Phi'\Sigma_\Phi'D_\Phi'^T$ by singular value decomposition of $V_\Phi$, wherein $U_\Phi'$ is the eigenvectors matrix, $E_\Phi'$, is the diagonal matrix, $D_\Phi'$ is the corresponding right-singular matrix;

substituting, using the processor, $V_\Phi$ into the Equation (2) to obtain:

$$\left[\sqrt{\frac{N-1}{N(N-2)}}(\Phi(x_1)-\tilde{m}_\Phi)\sqrt{\frac{1}{N-2}}\Phi(\tilde{X})\right] = \left[\frac{1}{h_\Phi}\sqrt{\frac{N-1}{N(N-2)}}[\Phi(x_1)-\Phi(\tilde{X})B]\Phi(\tilde{X})\tilde{A}\right] \times$$

equation (9)

$$U'_\Phi \Sigma'_\Phi D'^T_\Phi \begin{bmatrix} 1 & 0^T \\ 0_{N-1} & \tilde{D}_\Phi \end{bmatrix}^T$$

$$= \Phi([x_1 \quad \tilde{X}]) \begin{bmatrix} \frac{1}{h_\Phi}\sqrt{\frac{N-1}{N(N-2)}} & 0^T \\ -\frac{1}{h_\Phi}\sqrt{\frac{N-1}{N(N-2)}}B & \tilde{A} \end{bmatrix} \times$$

$$U'_\Phi \Sigma'_\Phi D'^T_\Phi \begin{bmatrix} 1 & 0^T \\ 0_{N-1} & \tilde{D}_\Phi \end{bmatrix}^T$$

$$= \Phi([\tilde{X} \quad x_1]) \begin{bmatrix} \tilde{A} & -\frac{1}{h_\Phi}\sqrt{\frac{N-1}{N(N-2)}}B \\ 0^T & \frac{1}{h_\Phi}\sqrt{\frac{N-1}{N(N-2)}} \end{bmatrix} \times$$

$$U'_\Phi \Sigma'_\Phi D'^T_\Phi \begin{bmatrix} 1 & 0^T \\ 0_{N-1} & \tilde{D}_\Phi \end{bmatrix}^T$$

where the main factors P of $C^F$ can be expressed as $$P = \Phi([x_1 \quad \tilde{X}]) \begin{bmatrix} \frac{1}{h_\Phi}\sqrt{\frac{N-1}{N(N-2)}} & 0^T \\ -\frac{1}{h_\Phi}\sqrt{\frac{N-1}{N(N-2)}}B & \tilde{A} \end{bmatrix} U'_\Phi$$

$$= \Phi(X) \begin{bmatrix} \frac{1}{h_\Phi}\sqrt{\frac{N-1}{N(N-2)}} & 0^T \\ -\frac{1}{h_\Phi}\sqrt{\frac{N-1}{N(N-2)}}B & \tilde{A} \end{bmatrix} U'_\Phi$$

Equation (10)

where since $P=\Phi(X)A$, Equation (11) can be obtained $$A = \begin{bmatrix} \frac{1}{h_\Phi}\sqrt{\frac{N-1}{N(N-2)}} & 0^T \\ -\frac{1}{h_\Phi}\sqrt{\frac{N-1}{N(N-2)}}B & \tilde{A} \end{bmatrix} U'_\Phi$$

the Equation (11)

where, from the Equation (11), $\tilde{A}$ can be calculated:

$$\begin{bmatrix} \frac{1}{h_\Phi}\sqrt{\frac{N-1}{N(N-2)}} & 0^T \\ -\frac{1}{h_\Phi}\sqrt{\frac{N-1}{N(N-2)}}B & \tilde{A} \end{bmatrix} = A(U'_\Phi)^{-1}$$

where after the main factors P is obtained from the initial monitoring model of the continuous annealing process in the Step 2, the score vector $t \in R^r$ in the feature space of the continuous annealing process can be obtained $$t = P^T[\Phi(x_{new}) - m_\Phi]$$

Equation (12)

$$= A^T \Phi(X)^T \left[\Phi(x_{new}) - \frac{1}{N}\Phi(X)1_N\right]$$

$$= A^T \left[k(X, x_{new}) - \frac{1}{N}K(X)1_N\right]$$

where $P=[p_1, p_2, \ldots, p_r]$, r is the number of the retaining nonlinear principal component, $k(X,x_{new})$ indicates the inner product of the sample matrix X and the new sample $x_{new}$ in the continuous annealing process; $T^2$ and SPE statistics of the new samples $x_{new}$ are calculated by Equations (13) and (14)

$$T_1^2 = t^T \Lambda^{-1} t$$

the Equation (13)

$$SPE_1 = [\Phi(x_{new}) - m_\Phi]^T (I - PP^T)[\Phi(x_{new}) - m_\Phi]$$

the Equation (14)

where $\Lambda$ is the eigenvalues matrix of the principal component, $T^2$ statistic satisfies the F distribution:

$$T^2 = \frac{r(N^2-1)}{N(N-r)} F_{r,N-r}$$

wherein N is the number of the sample, r is the number of the retaining principal component, the upper limit of the $T^2$ statistics is $$T_\beta^2 = \frac{r(N^2-1)}{N(N-r)} F_{r,N-r,\beta}$$

Equation (15)

wherein $\beta$ is the confidence level, while the Q statistic meets the $\chi^2$ distribution, the control upper limit is $$Q_\beta = g\chi^2(h)$$

Equation (16)

wherein, $g=\rho^2/2\mu$, $h=2\mu^2/\rho^2$, $\mu$ and $\rho^2$ indicate the sample mean and variance corresponding Q statistic; if $T_1^2$ and $SPE_1$ are greater than their respective confidence, an alarm occurs, which indicates the continuous annealing process anomalies occur; otherwise go to the Step 3.

3. The method as claimed in claim 1, wherein the Step 3 of updating the initial monitoring model of the continuous annealing process built in the Step 2 and calculating the principal factor $\hat{P}$ of the fault in the updated continuous annealing process model by the RKPCA includes:

letting, using the processor, $x_{new}$ be new samples in the continuous annealing process and be capable of being used, $\Phi(x_{new})$ be the new samples $x_{new}$'s projection in the feature space in the continuous annealing process, $\Phi(X_{new}) = \Phi([\tilde{X} \ x_{new}])$ be the samples matrix's projection in the feature space in the updated continuous annealing process, the mean matrix $\hat{m}_\Phi$ of $\Phi(X_{new})$ and covariance matrix $C^F$ are given by respectively $$\hat{m}_\Phi = \frac{1}{N}\Phi([\tilde{X} \ x_{new}])1_N = \frac{N-1}{N}\tilde{m}_\Phi + \frac{1}{N}\Phi(x_{new}) \quad \text{Equation (17)}$$

$$\hat{C}^F = \frac{1}{N-1}\Phi([\tilde{X} \ x_{new}])\Phi([\tilde{X} \ x_{new}])^T \quad \text{Equation (18)}$$

$$= \frac{N-2}{N-1}\left[\sqrt{\frac{N-1}{N(N-2)}}(\Phi(x_{new}) - \tilde{m}_\Phi) \ \sqrt{\frac{1}{N-2}}\Phi(\tilde{X})\right] \times$$

$$\left[\sqrt{\frac{N-1}{N(N-2)}}(\Phi(x_{new}) - \tilde{m}_\Phi) \ \sqrt{\frac{1}{N-2}}\Phi(\tilde{X})\right]^T$$

where from the Equations (2) to (9), the following can be obtained $$V'_\Phi = \begin{bmatrix} \Sigma_\Phi & \tilde{A}\tilde{A}^T\sqrt{\frac{N-1}{N(N-2)}}\left(k(\tilde{X}, x_{new}) - \frac{1}{N-1}K(\tilde{X})1_{N-1}\right) \\ 0^T & h'_\Phi \end{bmatrix}$$

$V_\Phi' = U_\Phi'' \Sigma_\Phi'' D_\Phi''^T$ can be further obtained by singular value decomposition of $V_\Phi'$, and thus the main factors $\hat{P}$ and the engenvalues matrix $\hat{\Lambda}$ of $\hat{C}^F$ can be obtained $$\hat{P} = \Phi([\tilde{X} \ x_{new}])\begin{bmatrix} \tilde{A} & -\frac{1}{h'_\Phi}\sqrt{\frac{N-1}{N(N-2)}}B' \\ 0^T & \frac{1}{h'_\Phi}\sqrt{\frac{N-1}{N(N-2)}} \end{bmatrix} \quad \text{Equation (19)}$$

$$U_\Phi'' = \Phi(X_{new})\hat{A}$$

$$\hat{\Lambda} = \frac{N-2}{N-1}\Sigma_\Phi''^2 \quad \text{Equation (20)}$$

where the regulating factor of the main factors for the updating monitoring model in the continuous annealing process $$h'_\Phi = \frac{N-1}{N(N-2)}\sqrt{1 - 2B'^T k(\tilde{X}, x_{new}) + B'^T K(\tilde{X})B'} \quad \text{Equation (21)}$$

where the correcting matrix of the main factors for the updating monitoring model in the continuous annealing process $$B' = \frac{1}{N-1}1_{N-1} + \tilde{A}\tilde{A}^T\left(k(\tilde{X}, x_{new}) - \frac{1}{N-1}K(\tilde{X})1_{N-1}\right) \quad \text{Equation (22)}$$

wherein $k(\tilde{X}, x_{new})$ indicates the inner product of the middle matrix $\tilde{X}$ and the new sample $x_{new}$.

* * * * *